United States Patent
Bridgeman et al.

(10) Patent No.: US 9,314,619 B2
(45) Date of Patent: Apr. 19, 2016

(54) CONNECTOR APPARATUS FOR A MEDICAL DEVICE

(71) Applicant: Greatbatch Ltd., Clarence, NY (US)

(72) Inventors: Elliot Bridgeman, Big Lake, MN (US); Lawrence Kane, St. Paul, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/483,233

(22) Filed: Sep. 11, 2014

(65) Prior Publication Data

US 2015/0079836 A1    Mar. 19, 2015

Related U.S. Application Data

(60) Provisional application No. 61/879,228, filed on Sep. 18, 2013.

(51) Int. Cl.
| | |
|---|---|
| H01R 13/33 | (2006.01) |
| A61N 1/05 | (2006.01) |
| H01R 24/58 | (2011.01) |
| A61N 1/375 | (2006.01) |
| H01R 107/00 | (2006.01) |

(52) U.S. Cl.
CPC ............... *A61N 1/056* (2013.01); *H01R 24/58* (2013.01); *A61N 1/3752* (2013.01); *H01R 13/33* (2013.01); *H01R 2107/00* (2013.01); *H01R 2201/00* (2013.01); *H01R 2201/12* (2013.01)

(58) Field of Classification Search
USPC ............ 439/840, 841, 379, 909, 668; 607/37
See application file for complete search history.

(56) References Cited

U.S. PATENT DOCUMENTS

| | | | |
|---|---|---|---|
| 4,603,696 A | 8/1986 | Cross et al. | |
| 4,712,557 A | 12/1987 | Harris | |
| 7,195,523 B2 * | 3/2007 | Naviaux | A61N 1/3752 439/668 |
| 7,769,459 B2 * | 8/2010 | Balsells | A61N 1/3752 607/37 |
| 8,480,437 B2 | 7/2013 | Dilmaghanian et al. | |
| 8,494,636 B2 | 7/2013 | Smith et al. | |
| 2006/0161215 A1 * | 7/2006 | Naviaux | A61N 1/3752 607/37 |
| 2006/0224208 A1 * | 10/2006 | Naviaux | A61N 1/3752 607/37 |
| 2008/0246231 A1 | 10/2008 | Sjostedt et al. | |
| 2009/0017668 A1 | 1/2009 | Deininger et al. | |

* cited by examiner

*Primary Examiner* — Tho D Ta
(74) *Attorney, Agent, or Firm* — Michael P. Horvath

(57) ABSTRACT

In various examples, a connector apparatus includes at least one connector including an integral conductor and an encapsulation housing. The at least one connector includes a contact portion and a tail portion, wherein the contact portion is configured to selectively accept and electrically couple to a therapy delivery element. The tail portion extends outwardly from the contact portion. The encapsulation housing at least partially surrounds at least some of the contact portion of the conductor. The encapsulation housing includes an inner surface, wherein at least some of the contact portion of the conductor extends from the inner surface of the encapsulation housing. With a contact of the therapy delivery element disposed within the encapsulation housing, the conductor is configured to contact and electrically couple with the contact of the therapy delivery element.

20 Claims, 3 Drawing Sheets

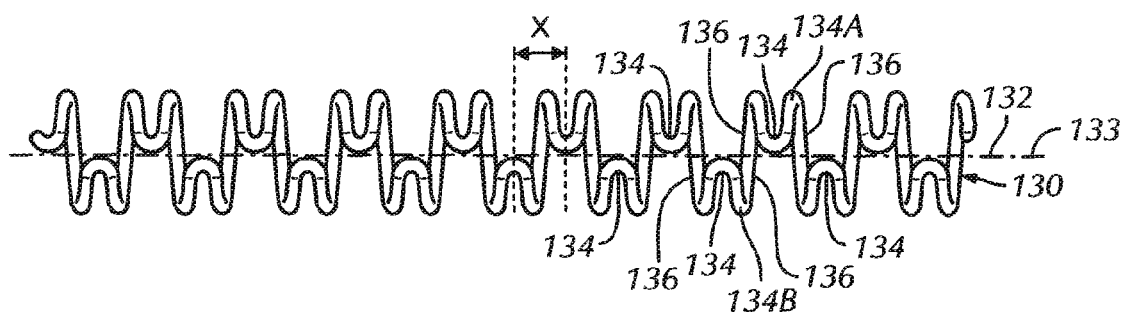
FIG. 7
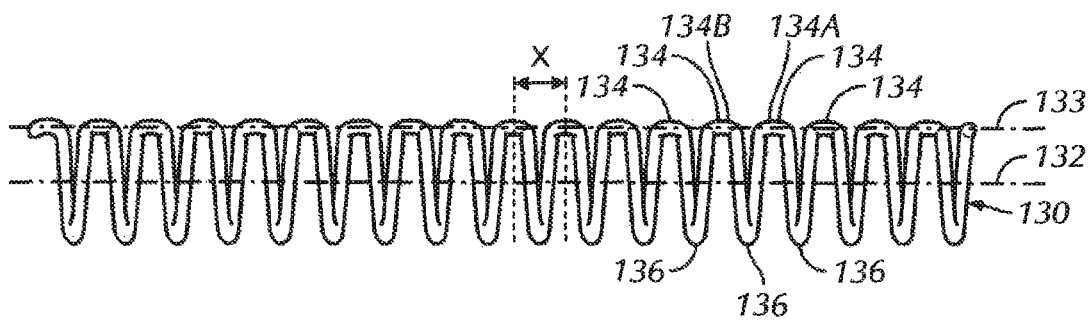
FIG. 8
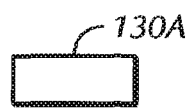  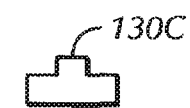 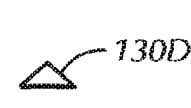
FIG. 9A  FIG. 9B  FIG. 9C  FIG. 9D
 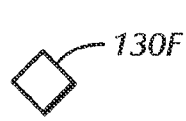 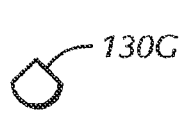 
FIG. 9E  FIG. 9F  FIG. 9G  FIG. 9H

CONNECTOR APPARATUS FOR A MEDICAL DEVICE

CROSS REFERENCE TO RELATED APPLICATIONS

This application claims the benefit of priority to U.S. Provisional Application Ser. No. 61/879,228, filed on Sep. 18, 2013, entitled "CONNECTOR APPARATUS," which is incorporated by reference herein in its entirety.

BACKGROUND

The present invention relates to a connector apparatus, and more specifically relates to a connector apparatus for electrically connecting a therapy delivery element to a device.

In some connector apparatuses, multiple welds are required for each contact. With multiple contacts in some connector apparatuses (for instance, eight or twelve connectors), the number of welds required for a header can become very large. Due to the number of welds required per device, the relatively small scale of the connector apparatus, and/or the relative delicacy of the electronics associated with the device for which the connector apparatus is being used, it is fairly common to damage or even ruin a connector apparatus or even a device on which the connector apparatus is being attached during the welding process, such as with an improper weld, excessive heat to the electronics, or other human error involved in the manufacture of the device. Moreover, the individual contacts themselves can be very small and also quite complex components, providing additional areas in which to introduce possible defects into the connector apparatus and, in turn, increasing the likelihood of damaging or ruining a connector apparatus or a device. Such losses can add up quickly given the generally high costs of the device and the connector apparatus.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used with respect to connectors for use in connecting devices together, such as, but not limited to, connecting a therapy delivery element to a stimulation device. The present inventors have recognized the present subject matter can be used to relatively easily and relatively inexpensively produce individual connectors and, in turn, a connector apparatus. In some examples, the connector is versatile in that it is able to expand and contract to make electrical contact with a variety of implantable therapy delivery devices. In some examples, the connector of the present subject matter includes fewer welds than other connectors, such that there is smaller risk of human error (for instance, making an improper or otherwise substandard weld) in producing the connector or the connector apparatus or attaching the connector or the connector apparatus to a device. To better illustrate the apparatuses, systems, and methods described herein, a non-limiting list of examples is provided here:

Example 1 can include subject matter that can include a connector apparatus including at least one connector including an integral conductor and an encapsulation housing. The conductor includes a contact portion and a tail portion, wherein the contact portion is configured to selectively accept and electrically couple to a therapy delivery element. The tail portion extends outwardly from the contact portion. An encapsulation housing at least partially surrounds at least some of the contact portion of the conductor. The encapsulation housing includes an inner surface, wherein at least some of the contact portion of the conductor extends from the inner surface of the encapsulation housing. With a contact of the therapy delivery element disposed within the encapsulation housing, the contact portion of the conductor is configured to contact and electrically couple with the contact of the therapy delivery element.

In Example 2, the subject matter of Example 1 is optionally configured such that the encapsulation housing includes a substantially annular shape. The inner surface of the encapsulation housing forms a passage through the encapsulation housing. The passage is configured to accept at least a portion of the therapy delivery element.

In Example 3, the subject matter of Example 2 is optionally configured such that the contact portion of the conductor extends at least 180 degrees around the passage of the encapsulation housing.

In Example 4, the subject matter of any one of Examples 1-3 is optionally configured such that the connector apparatus includes more than one connector, wherein the passage of each of the connectors is generally aligned with one another along a connector apparatus axis.

In Example 5, the subject matter of Example 4 optionally includes a connector housing engaged with the more than one connector. The connector housing is configured to maintain a spacing and position of the more than one connector within the connector apparatus.

In Example 6, the subject matter of Example 5 is optionally configured such that the connector housing is disposed around the more than one connector.

In Example 7, the subject matter of any one of Examples 5-6 is optionally configured such that at least a portion of the connector housing is overmolded with the more than one connector.

In Example 8, the subject matter of any one of Examples 5-7 is optionally configured such that at least a portion of the connector housing is laminated over the more than one connector.

In Example 9, the subject matter of any one of Examples 1-8 is optionally configured such that the conductor is formed from a wire form including a substantially circular shape when viewed from an end.

In Example 10, the subject matter of Example 9 is optionally configured such that the wire form includes a wave-like pattern when flattened.

In Example 11, the subject matter of any one of Examples 9-10 is optionally configured such that the wire form includes substantially U-shaped portions each extending part way around an imaginary cylinder, such that the wire form forms a substantially tubular shape.

In Example 12, the subject matter of Example 11 is optionally configured such that the substantially U-shaped portions are disposed in an alternating pattern, with a first substantially U-shaped portion extending in a first direction and an adjacent second substantially U-shaped portion extending in a second direction.

In Example 13, the subject matter of Example 12 is optionally configured such that the first substantially U-shaped portion and the second substantially U-shaped portion are connected to each other by an integral curved connecting portion.

In Example 14, the subject matter of any one of Examples 12-13 is optionally configured such that crests of the adjacent substantially U-shaped portions extend to an imaginary axis spaced radially outwardly from a longitudinal axis of the wire form.

In Example 15, the subject matter of any one of Examples 1-14 is optionally configured such that at least a portion of the encapsulation housing is overmolded with the contact portion of the conductor.

In Example 16, the subject matter of any one of Examples 1-15 is optionally configured such that the tail portion is formed to substantially align with a device wire location, the tail portion configured to be electrically coupled to the device wire location.

Example 17 can include, or can optionally be combined with any one of Examples 1-16 to include subject matter that can include a connector apparatus including a plurality of connectors. Each connector includes an integral conductor including a contact portion and a tail portion, wherein the contact portion is configured to selectively accept and electrically couple to a therapy delivery element. The tail portion extends outwardly from the contact portion. An encapsulation housing at least partially surrounds at least some of the contact portion of the conductor. The encapsulation housing includes an inner surface, wherein at least some of the contact portion of the conductor extends from the inner surface of the encapsulation housing. With a contact of the therapy delivery element disposed within the encapsulation housing, the contact portion of the conductor is configured to contact and electrically couple with the contact of the therapy delivery element. A connector housing is engaged with the plurality of connectors. The connector housing is configured to maintain a spacing and position of the plurality of connectors within the connector apparatus, wherein the passage of each of the plurality of connectors is generally aligned with one another along a connector apparatus axis.

In Example 18, the subject matter of Example 17 is optionally configured such that the connector housing is disposed around the plurality of connectors, at least a portion of the connector housing being overmolded with or laminated over the plurality of connectors.

In Example 19, the subject matter of any one of Examples 17-18 is optionally configured such that the conductor is formed from a wire form including a substantially circular shape when viewed from an end. The wire form includes substantially U-shaped portions each extending part way around an imaginary cylinder, such that the wire form forms a substantially tubular shape. The substantially U-shaped portions are disposed in an alternating pattern, with a first substantially U-shaped portion extending in a first direction and an adjacent second substantially U-shaped portion extending in a second direction.

In Example 20, the subject matter of any one of Examples 17-19 is optionally configured such that the tail portion is formed to substantially align with a device wire location. The tail portion is configured to be electrically coupled to the device wire location.

BRIEF DESCRIPTION OF THE DRAWINGS

FIG. 7 is a top view of a wire form for use in a connector apparatus in accordance with at least one example of the invention.

FIG. 8 is a side view of a wire form for use in a connector apparatus in accordance with at least one example of the invention.

FIGS. 9A-9H are cross-sectional views of various examples of wire for use in a connector apparatus in accordance with at least one example of the invention.

DETAILED DESCRIPTION

The present patent application relates to a connector apparatus. In various examples, as described herein, the connector apparatus is configured to allow electrical attachment of a therapy delivery element to a device. In some examples, the connector apparatus can be used to implantably connect a therapy delivery element to a device. In some examples, the therapy delivery element includes an electrical lead including a pacing or defibrillation lead, a stimulation lead, or a sensing lead.

Figure 1:
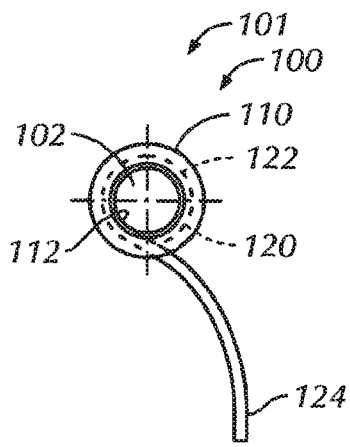
FIG. 1 is an end view of a connector in accordance with at least one example of the invention.
Figure 2:
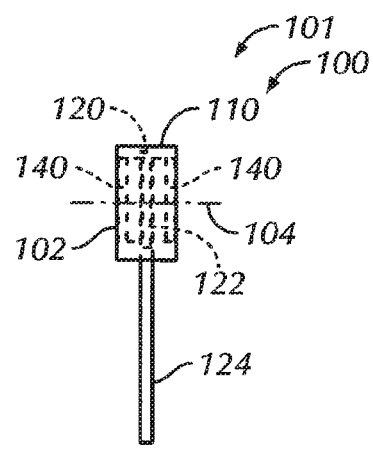
FIG. 2 is a side view of a connector in accordance with at least one example of the invention.

Referring to FIGS. 1 and 2, in some examples, a connector apparatus 100 is configured to electrically couple a therapy delivery element to a device, such as, but not limited to, pulse generator circuitry. In some examples, the connector apparatus 100 includes one connector 101. In other examples, a connector apparatus includes more than one connector 101, as is described in more detail herein. In some examples, the connector 101 includes an integral conductor 120 including a contact portion 122 and a tail portion 124. That is, in some examples, the contact portion 122 and the tail portion 124 are formed from the same piece of material such that no attachment of the contact portion 122 to the tail portion 124 is necessary. In some examples, the contact portion 122 is configured to selectively accept and electrically couple to a therapy delivery element. In some examples, the tail portion 124 extends outwardly from the contact portion 122. As is described herein, the tail portion 124, in some examples, can be formed into various shapes to allow for connection with a lead or other portion of a device, such as, for instance, pulse generator circuitry.

In some examples, the connector 101 includes an encapsulation housing 110 at least partially surrounding at least some of the contact portion 122 of the conductor 120. In some examples, at least a portion of the encapsulation housing 110 is overmolded with the contact portion 122 of the conductor 120. In some examples, the encapsulation housing 110 includes an inner surface 112, wherein at least some of the contact portion 122 of the conductor 120 extends from the inner surface 112 of the encapsulation housing 110. In this way, at least some of the contact portion 122 is exposed to make electrical contact with another device. The tail portion 124, in some examples, is formed to substantially align with a device wire location, the tail portion 124 being configured to be electrically coupled to the device wire location. In some examples, with a contact of the therapy delivery element disposed within the encapsulation housing 110, the contact portion 122 of the conductor 120 is configured to contact and electrically couple with the contact of the therapy delivery element. In some examples, the encapsulation housing 110 includes a substantially annular shape, the inner surface 112 of the encapsulation housing 110 forming a passage 102 through the encapsulation housing 110. In some examples, the passage 102 extends through the encapsulation housing 110 along a housing axis 104. In some examples, the passage 102 is configured to accept at least a portion of the therapy delivery element. In some examples, the contact portion 122 of the conductor 120 extends at least 180 degrees around the passage 102 of the encapsulation housing 110. In further examples, the contact portion 122 of the conductor 120 extends substantially 360 degrees around the passage 102 of the encapsulation housing 110. In still further examples, the contact portion 122 of the conductor 120 extends more than 300 degrees but less than 360 degrees around the passage 102 of the encapsulation housing 110.

Figure 6:
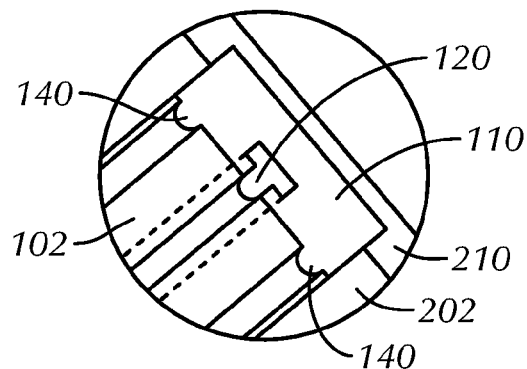
FIG. 6 is an enlarged sectional view of the area 6 of FIG. 5.
Figure 5:
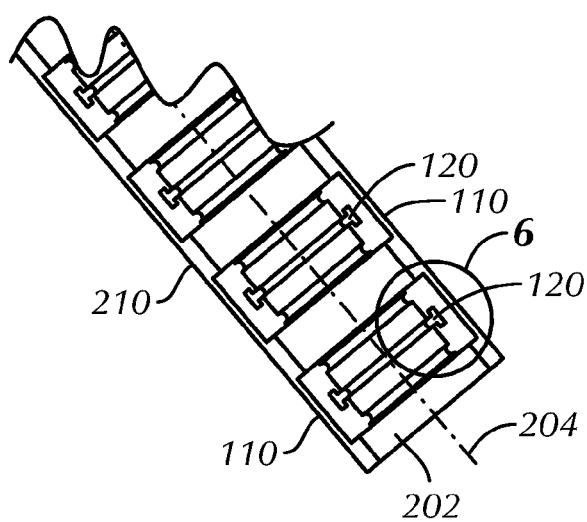
FIG. 5 is a cross-sectional view of the connector apparatus of FIG. 4 taken along line 5-5.

Referring to FIGS. 2 and 6, in some examples, the connector 101 includes at least one seal 140. In some examples, the connector 101 includes two seals 140 along the inner surface 112 of the encapsulation housing 110, with one seal 140 being disposed on either side of the contact portion 122 of the conductor 120. In some examples, the one or more seals 140 inhibit moisture, fluids, contaminants, or other materials from entering the passage 102 and potentially becoming disposed within the passage 102 and/or between the contact portion 122 and the contact of the therapy delivery element to help limit degradation of the integrity of the electrical connection between the contact portion 122 and the contact of the therapy delivery element due to incursion of moisture, fluids, contaminants, or other materials within the passage 102 of the encapsulation housing 110. In some examples, the one or more seals 140 are integrally formed with the encapsulation housing 110. That is, in some examples, the one or more seals 140 can be molding features of the encapsulation housing 110 formed during overmolding of the encapsulation housing 110 with the contact portion 122. In other examples, the one or more seals 140 can be separately formed from the encapsulation housing 110 and attached to the inner surface 112 of the encapsulation housing 110 after forming of the encapsulation housing 110.

Referring to FIGS. 3-6, in some examples, a connector apparatus 200 includes more than one connector 101, wherein the passage 102 of each of the connectors 101 is generally aligned with one another along a connector apparatus axis 204. In some examples, the housing axes 104 of the connectors 101 are substantially aligned along the connector apparatus axis 204. In the example shown in FIG. 3, the connector apparatus 200 includes twelve connectors 101. In other examples, the connector apparatus can include more or less than twelve connectors, depending upon, for instance, the number of contacts on the particular therapy delivery element that is to be used with the connector apparatus. In some examples, the connector apparatus 200 can be used in a header for a device. In some examples, the connector apparatus 200 can be used in a header for a pulse generator. In some examples, more than one connector apparatus 200 can be used in a header for a device. In further examples, the connector apparatuses 200 can be stacked next to and/or on top of one another to allow for electrical connection of the header to more than one device, such as more than one therapy delivery element.

In some examples, the connector apparatus 200 includes a connector housing 210 engaged with the connectors 101. In some examples, the connector housing 210 is configured to maintain a spacing and position of the connectors 101 within the connector apparatus 200. For instance, in some examples, depending on the spacing of contacts on the device (for instance, a therapy delivery element) to be electrically coupled within the connector apparatus 200, the connector housing 210 can be shaped and sized to maintain each of the connectors 101 in a position and orientation in order to electrically couple with each of the corresponding contacts of the device (for instance, a therapy delivery element). In some examples, the connector housing 210 is disposed around the connectors 101. In some examples, the connector housing 210 includes a bore 202 disposed along the connector apparatus axis 204. The passages 102 of the connectors 101, in some examples, are aligned with the bore 202, such that an end of a device, such as a therapy delivery element, is insertable within the bore 202 to allow alignment of the contacts of the therapy delivery element within each of the corresponding passages 102 of the contacts 101, thereby allowing electrical connection of the therapy delivery element with the device (pulse generator circuitry, for instance) to which the tail portions 124 of the conductors 120 connect. The connector housing 210 can be formed in various ways. In some examples, at least a portion of the connector housing 210 is overmolded with the connectors 101. In some examples, at least a portion of the connector housing 210 is laminated over the connectors 101. In some examples, at least a portion of the connector housing 210 is formed and snapped together over the connectors 101. In other examples, other manners of forming the connector housing 210 at least partially around the connectors 101 are contemplated.

Figure 3:
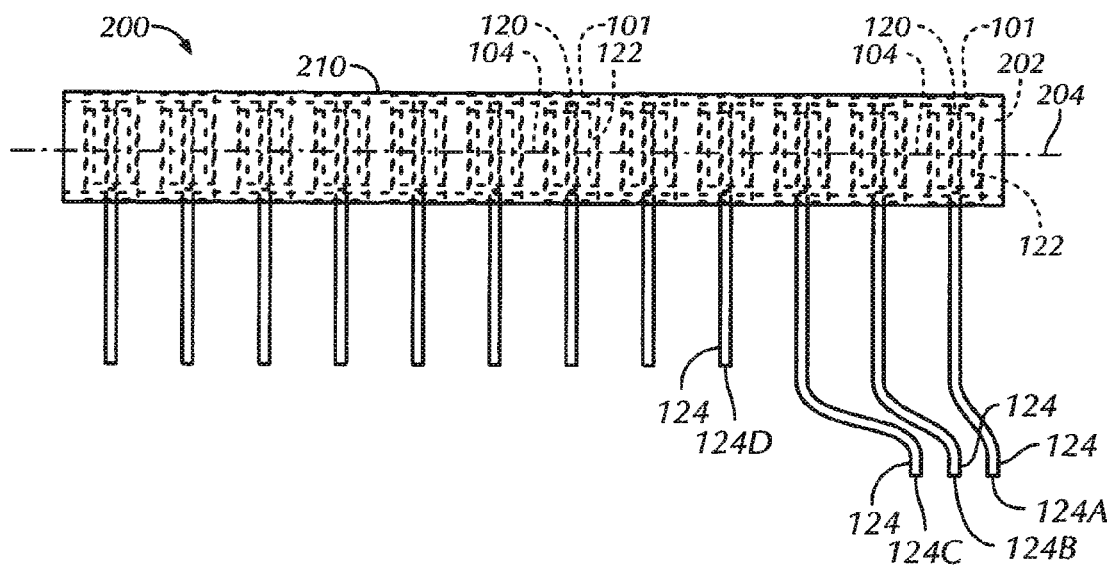
FIG. 3 is a side view of a connector apparatus in accordance with at least one example of the invention.
Figure 4:
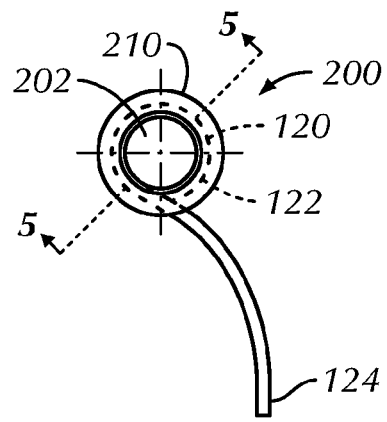
FIG. 4 is an end view of a connector apparatus in accordance with at least one example of the invention.

Referring now to FIGS. 1-3, the one or more tail portions 124 of the connector apparatus 100, 200 can be configured in various ways. In some examples, the one or more tail portions 124 are shaped so that the one or more tail portions 124 can be coupled to a corresponding one or more contacts within a device, such as pulse generator circuitry. That is, the one or more tail portions 124 are formed to extend to and electrically couple with the one or more contacts within the device to which the connector apparatus 100, 200 is being attached. In some examples, because the one or more tail portions 124 are integrally formed with the one or more contact portions 122 and do not have to be welded or otherwise attached to the one or more contact portions 122, the number of weld points or other connections necessary for the device is reduced from previous connection systems. Based on the path between the contact portion 122 and the contact within the device, the tail portion 124 can be sized and formed to extend to the contact within the device with the connector apparatus 100, 200 in place with respect to the device. In some examples, the one or more tails 124 of the connector apparatus 100, 200 can be pre-formed, such that the one or more tails 124 need only be welded or otherwise attached to the corresponding one or more contacts of the device. Referring specifically to FIG. 3, examples of tail portions 124A, 124B, 124C, 124D formed in various configurations are shown. It should be understood that configurations other than the tail portions 124A, 124B, 124C, 124D are contemplated herein, depending upon the path between the contact portion 122 and the corresponding contact of the device.

Referring to FIGS. 7 and 8, in some examples, the conductor 120 is formed from a wire form 130 including a substantially circular shape when viewed from an end, the wire form 130 including a longitudinal axis 132 and forming a substantially tubular shape generally centered along the longitudinal axis 132. In other examples, the conductor can be formed into shapes other than a substantially circular shape when viewed from an end, such as, but not limited to a substantially square shape, a substantially rectangular shape, a substantially triangular shape, a substantially polygonal shape, a star or star-like shape, a substantially elliptical shape, a lobed or flower-like shape, or the like.

In some examples, the wire form 130 includes a wave-like pattern when flattened. In some examples, the wire form 130 includes a wave-like pattern when flattened, the wave-like pattern including peaks. The wave-like pattern can take different forms in various examples, such as, for instance, a substantially sinusoidal wave pattern, a substantially triangular or saw-tooth wave pattern, a substantially square wave pattern, or the like, or a combination of two or more wave patterns.

In some examples, the wire form 130 includes substantially U-shaped portions 134. In some examples, the substantially U-shaped portions 134 form the peaks of the wave-like pattern of the wire form 130 with the wire form 130 flattened. In some examples, with the wire form 130 in the substantially tubular shape, the substantially U-shaped portions 134 each extend part way around an imaginary cylinder. In some examples, the substantially U-shaped portions 134 are in an alternating pattern, with a first substantially U-shaped portion 134A extending generally downwardly (as seen in FIG. 7) and an adjacent second substantially U-shaped portion 134B extending generally upwardly (as seen in FIG. 7), the first substantially U-shaped portion 134A and the second substantially U-shaped portion 134B being connected to each other by an integral curved connecting portion 136. In some examples, crests of the adjacent substantially U-shaped portions 134A, 134B extend to an imaginary axis 133 spaced radially outwardly from the longitudinal axis 132 of the wire form 130. In other examples, the crests of the adjacent substantially U-shaped portions 134A, 134B cross the imaginary axis 133 and overlap one another. In still other examples, the crests of the adjacent substantially U-shaped portions 134A, 134B are spaced from the imaginary axis 133 and do not overlap one another.

In some examples, the wire form 130 is drawn or extruded into wire and then formed into the pattern, for instance, formed into the wavelike pattern and then further formed into the circular shape when viewed from the end. In some examples, the wire form 130 can be cut from stock. For instance, in some examples, the wire form 130 can be laser cut from a sheet of material and then formed into a substantially tubular (or other) form for use within the connector 101. In further examples, other ways of manufacturing the wire form 130 are contemplated.

In some examples, the wire form 130 can include a length longer than is needed within a connector, such as the connector 101 described herein. In such examples, the wire form 130 can be cut into one or more lengths sufficient to form a conductor 120 for use with the connector 101. In some examples, the wire form 130 is cut to a length sufficient to form the contact portion 122 and the tail portion 124. For instance, the wire form 130, in some examples, can be cut to include a sufficient length to form the contact portion 122 of a sufficient circumference and length, as well as the tail portion 124 of a sufficient length to form into a shape to extend between and electrically couple the contact portion 122 with the device, such as, for instance, the pulse generator circuitry. Depending upon the path along which the tail portion 124 is to extend, the one or more tail portions 124 can be formed from the wire form 130 into various shapes (see, for example, the formed tail portions 124A, 124B, 124C, 124D of FIG. 3). Depending upon the desired shape of the tail portion 124, in some examples, a section of the wire form 130 can be cut off, with a portion of the section of the wire form 130 being substantially straightened out and formed into the desired shape of the tail portion 124, and the remainder of the section of the wire form 130 being used for the contact portion 122 of the conductor 120. In some examples, the remainder of the section of the wire form 130 used for the contact portion 122 can include one coil X of the wire form 130. In some examples, the remainder of the section of the wire form 130 used for the contact portion 122 can include less than one coil X of the wire form 130. In other examples, the remainder of the section of the wire form 130 used for the contact portion 122 can include more than one coil X of the wire form 130. In some examples, the remainder of the section of the wire form 130 used for the contact portion 122 is compressed in a lengthwise direction from what is shown in FIGS. 7 and 8, for instance, to fit within a connector of limited width. It is noted that the term coil is used herein to describe a length of the wire form 130 of between adjacent peaks of the wavelike pattern of the wire form 130. In some examples, the wavelike pattern of the wire form 130, since it is not a complete helix, allows for expansion and/or contraction of the contact portion 122 in order to make electrical contact with a variety of contacts of devices, such as, for instance, therapy delivery elements.

Referring to FIGS. 9A-9H, various examples of cross sections of the wire form 130 are shown. The wire form 130, in some examples, can be drawn, extruded, cut, or otherwise formed into various cross sections. For instance, in various examples, the wire form 130 can include a rectangular cross section (FIG. 9A), a square cross section (FIG. 9B), a T-shaped cross section (FIG. 9C), a triangular cross section (FIG. 9D), a circular cross section (FIG. 9E), a diamond-shaped cross section (FIG. 9F), tear-drop-shaped cross section (FIG. 9G), or a hemispherical cross section (FIG. 9H). It should be understood that, in other examples, the wire form 130 is contemplated as having cross sections other than those shown in FIGS. 9A-9H, such as, but not limited to a cross-shaped cross section, an ovular cross section, an elliptical cross section, a semicircular cross section, a rhomboid cross section, a pentagonal cross section, a hexagonal cross section, or the like. In various examples, the shape of the cross section of the wire form 130 can enhance or facilitate one or more of forming of the wire form 130 into the desired shape for the conductor 120, flexibility of the contact portion 122, gripping of the contact portion 122, or the like.

In some examples, the connector apparatus 100, 200 can allow for tuning, varying, controlling, or otherwise determining of an insertion force for insertion of one or more contacts of a device (for instance, a therapy delivery element) into the connector apparatus 100, 200. By changing the shape and/or size of the wire form 130, in some examples, the force required to expand the wire form 130 and, in turn, the contact portion 122 of the conductor 120, can be altered, allowing for the insertion force to be tuned, varied, controlled, or otherwise determined based upon the shape and/or size of the wire form 130. In some examples, one or more material properties of the encapsulation housing 110 and/or the connector housing 210 disposed around the contact portion 122 of the connector 101 can also be used to tune, vary, control, or otherwise determine the insertion force. For instance, in some examples, a durometer of the encapsulation housing 110 and/or the connector housing 210 can affect the force required to expand the contact portion 122. In some examples, the encapsulation housing 110 and/or the connector housing 210 are formed from single durometer materials. In some examples, the encapsulation housing 110 and/or the connector housing 210 are formed from multiple durometer materials. In some examples, the encapsulation housing 110 and the connector housing 210 are formed from the same material. In other examples, the encapsulation housing 110 and the connector housing 210 are formed from different materials. In some examples, one or both of the encapsulation housing 110 and the connector housing 210 are formed from one or more rigid polymers, such as, but not limited to epoxy, urethane, or the like.

The present inventors have recognized various advantages of the subject matter described herein. For instance, in some examples, individual connectors and, in turn, a connector apparatus can be relatively easily and relatively inexpensively produced. In some examples, the connector is versatile in that it is able to expand and contract to make electrical contact with a variety of implantable therapy delivery devices. In some examples, the connector of the present subject matter includes fewer welds than other connectors, such that there is smaller risk of human error (for instance, making an improper or otherwise substandard weld) in producing the connector or the connector apparatus or attaching the connector or the connector apparatus to a device. While various advantages of the example apparatuses are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A connector apparatus for a medical device, the connector apparatus comprising:

at least one connector including:
an integral conductor including a contact portion and a tail portion, wherein the contact portion is configured to selectively accept and electrically couple to a therapy delivery element, the tail portion extending outwardly from the contact portion; and
an encapsulation housing at least partially surrounding at least some of the contact portion of the conductor, the encapsulation housing including an outer surface spaced from an inner surface, wherein at least some of the contact portion of the conductor extends inwardly from the inner surface of the encapsulation housing, and wherein, with a contact of the therapy delivery element disposed within the encapsulation housing, the contact portion of the conductor is configured to contact and electrically couple with the contact of the therapy delivery element, wherein the tail portion extends from within the encapsulation housing and outwardly past the outer surface of the encapsulation housing, and wherein the tail portion is configured to attach directly to a lead of the medical device.

2. The connector apparatus of claim 1, wherein the encapsulation housing includes a substantially annular shape, the inner surface of the encapsulation housing forming a passage through the encapsulation housing, the passage configured to accept at least a portion of the therapy delivery element.

3. The connector apparatus of claim 2, wherein the contact portion of the conductor extends at least 180 degrees around the passage of the encapsulation housing.

4. The connector apparatus of claim 1, wherein the connector apparatus includes more than one connector, wherein the passage of each of the connectors is generally aligned with one another along a connector apparatus axis.

5. The connector apparatus of claim 4, comprising a connector housing engaged with the more than one connector, the connector housing configured to maintain a spacing and position of the more than one connector within the connector apparatus.

6. The connector apparatus of claim 5, wherein the connector housing is disposed around the more than one connector.

7. The connector apparatus of claim 5, wherein at least a portion of the connector housing is overmolded with the more than one connector.

8. The connector apparatus of claim 5, wherein at least a portion of the connector housing is laminated over the more than one connector.

9. The connector apparatus of claim 1, wherein the conductor is formed from a wire form including a substantially circular shape when viewed from an end.

10. The connector apparatus of claim 9, wherein the wire form includes a wave-like pattern when flattened.

11. The connector apparatus of claim 9, wherein the wire form includes at least two substantially U-shaped portions, each U-shaped portion extending part way around an imaginary cylinder, such that the wire form forms a substantially tubular shape.

12. The connector apparatus of claim 11, wherein the substantially U-shaped portions are disposed in an alternating pattern, with a first substantially U-shaped portion extending in a first direction and an adjacent second substantially U-shaped portion extending in a second direction that is substantially opposite the first direction with respect to a longitudinal axis of the wire form.

13. The connector apparatus of claim 12, wherein the first substantially U-shaped portion and the second substantially U-shaped portion are connected to each other by an integral curved connecting portion.

14. The connector apparatus of claim 12, wherein crests of the adjacent substantially U-shaped portions extend to an imaginary axis spaced radially outwardly from a longitudinal axis of the wire form.

15. The connector apparatus of claim 1, wherein at least a portion of the encapsulation housing is overmolded with the contact portion of the conductor.

16. The connector apparatus of claim 1, wherein the tail portion is formed to substantially align with a device wire location, the tail portion configured to be electrically coupled to the device wire location.

17. A connector apparatus for a medical device, the connector apparatus comprising:
   a plurality of connectors, each connector including:
      an integral conductor including a contact portion and a tail portion, wherein the contact portion is configured to selectively accept and electrically couple to a therapy delivery element, the tail portion extending outwardly from the contact portion; and
      an encapsulation housing at least partially surrounding at least some of the contact portion of the conductor, the encapsulation housing including an outer surface spaced from an inner surface, wherein at least some of the contact portion of the conductor extends inwardly from the inner surface of the encapsulation housing, and wherein, with a contact of the therapy delivery element disposed within the encapsulation housing, the contact portion of the conductor is configured to contact and electrically couple with the contact of the therapy delivery element, wherein the tail portion extends from within the encapsulation housing and outwardly past the outer surface of the encapsulation housing, and wherein the tail portion is configured to attach directly to a lead of the medical device; and
   a connector housing engaged with the plurality of connectors, the connector housing configured to maintain a spacing and position of the plurality of connectors within the connector apparatus, wherein the passage of each of the plurality of connectors is generally aligned with one another along a connector apparatus axis.

18. The connector apparatus of claim 17, wherein the connector housing is disposed around the plurality of connectors, at least a portion of the connector housing being overmolded with or laminated over the plurality of connectors.

19. The connector apparatus of claim 17, wherein the conductor is formed from a wire form including a substantially circular shape when viewed from an end, the wire form including substantially U-shaped portions each extending part way around an imaginary cylinder, such that the wire form forms a substantially tubular shape, the substantially U-shaped portions being disposed in an alternating pattern, with a first substantially U-shaped portion extending in a first direction and an adjacent second substantially U-shaped portion extending in a second direction that is substantially opposite the first direction with respect to a longitudinal axis of the wire form.

20. The connector apparatus of claim 17, wherein the tail portion is formed to substantially align with a device wire location, the tail portion configured to be electrically coupled to the device wire location.

* * * * *